United States Patent [19]
Deckner

[11] Patent Number: 5,928,289
[45] Date of Patent: Jul. 27, 1999

[54] ANCHORING ROD USED PARTICULARLY IN PROSTHESES

[76] Inventor: André Georges Deckner, 5 Rue de l'Harmonie, Paris, France, 75015

[21] Appl. No.: 08/792,901

[22] Filed: Jan. 31, 1997

[30] Foreign Application Priority Data

Feb. 8, 1996 [FR] France .................................. 96 01541

[51] Int. Cl.$^6$ ...................................................... A61F 2/36
[52] U.S. Cl. .................................. 623/23; 623/18; 623/22
[58] Field of Search ................... 623/22, 23, 16, 623/18; 606/62, 66, 67, 72

[56] References Cited

U.S. PATENT DOCUMENTS

| | | | |
|---|---|---|---|
| 3,977,398 | 8/1976 | Burstein | 606/62 |
| 3,996,625 | 12/1976 | Noiles | 623/22 |
| 4,135,507 | 1/1979 | Harris | 606/64 |
| 4,644,668 | 5/1987 | Beck et al. | 623/23 |
| 4,944,759 | 7/1990 | Mallory et al. | 623/23 |
| 4,957,510 | 9/1990 | Cremascoli | 623/23 |
| 5,152,799 | 10/1992 | Lyons | 623/23 |
| 5,201,770 | 4/1993 | Sola | 623/23 |
| 5,258,035 | 11/1993 | Hoffman et al. | 623/23 |
| 5,370,695 | 12/1994 | Meuli et al. | 623/23 |
| 5,593,446 | 1/1997 | Kuoni | 623/23 |
| 5,702,484 | 12/1997 | Goymann et al. | 623/23 |

FOREIGN PATENT DOCUMENTS

| | | |
|---|---|---|
| 0 159 510 | 10/1985 | European Pat. Off. . |
| 0 382 428 | 8/1990 | European Pat. Off. . |
| 2 327 757 | 5/1977 | France . |
| 2 528 307 | 12/1983 | France . |
| 2 641 462 | 7/1990 | France . |
| 88 11 758 | 11/1988 | Germany . |
| 94 02 934 | 9/1994 | Germany . |

*Primary Examiner*—Michael J. Milano
*Assistant Examiner*—Tram A. Nguyen
*Attorney, Agent, or Firm*—Pearne, Gordon, McCoy & Granger LLP

[57] ABSTRACT

An anchoring rod includes a proximal zone and an axial anchoring zone having a plurality of sides arranged in a generally square cross-section and joining at least two pairs of cutting fins. Each pair of cutting fins includes two fins spaced by a recess having opposed sides. Each fin formed by a dihedron provided by the intersection of the adjacent sides of the anchoring zone and recess. The two most remote sides of the dihedra of the pair of fins form an angle of from 60° to 120°. This angular relationship is applicable to the extents of the remote sides extending a distance only in the order of one millimeter from the adjacent fin, the length being measured from each fin along the surfaces of the respective sides.

17 Claims, 4 Drawing Sheets

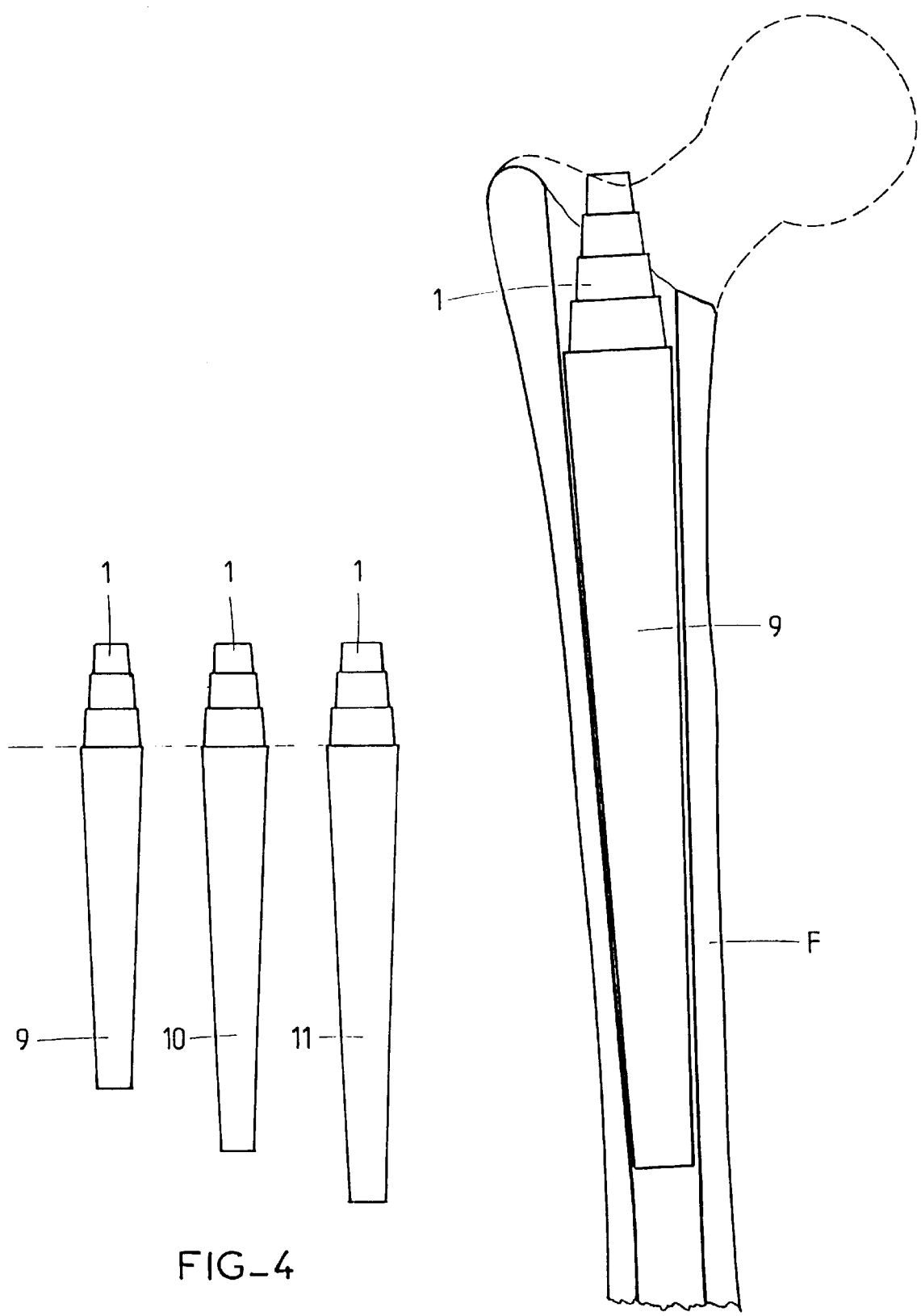
FIG_4
FIG_5

ANCHORING ROD USED PARTICULARLY IN PROSTHESES

BACKGROUND OF THE INVENTION

A prosthesis anchoring rod should become immobilized when put into position (primary immobilization) and over the course of time it should not become buried progressively deeper in the medullary channel of the bone, nor should it develop any play.

SUMMARY OF THE INVENTION

The invention related to an anchoring rod which has both these properties.

The anchoring rod according to the invention comprising a proximal zone and an anchoring zone having one axis is characterized in that the anchoring zone has at least two pairs of cutting fins, each fin being formed by a dihedron, the two most remote sides of the dihedra of each pair of fins forming between them an angle equal to from 60° to 120°, the directions of the sides being taken into consideration only over a distance of the order of one millimeter from the adjacent fins. In other words, the one millimeter length is measured from each fin 12a, 13a along the surfaces of the respective sides 4, 6 in a plane passing through the axis of the anchoring zone at a right angle.

As the fins have a cutting edge, they penetrate well into the bone when inserted, ensuring good primary immobilization.

However, as the angle between the two most remote sides of the dihedra of each pair of fins has the values given above, the surface facing the bone increases more than proportionally as the rod beings to be buried in the bone. An equilibrium is rapidly achieved in which the bone resists the tendency of the prosthesis to work in deeper.

Preferably, the fins extend substantially over the entire length of the anchoring zone, which also ensures better primary immobilization and ensures that pressure is uniformly distributed along the entire length of the bone.

Preferably, the fins are substantially parallel to the axis X'X", which also helps to distribute the pressure uniformly and thus reduces pain.

When the two nearest sides of the dihedra forming a pair of fins pass substantially through the axis, better resistance to rotational stresses is obtained, since, even if the rod is buried in the bone, it still remains fully in contact therewith, without any empty spaces, as would otherwise be the case.

To ensure better immobilization it is also a good idea if, viewed in section at right angles to the axis, the points or apexes corresponding to the fins are located on the same imaginary circle or, in other words, the apexes of the fins are equidistant from the axis as measured in a plane passing through the axis at a right angle. All the fins are then effective at the same time.

Even better distribution of pressure is achieved if, in cross section, each fin forms a constant angle with the axis, no matter where the section is taken. That is, the cross-sectional angular orientation of each fin relative to the axis remains constant along the length of the anchoring zone.

According to an improved feature of the invention, the longitudinal axis of the anchoring zone, instead of being rectilinear, is curved and extends along a logarithmic spiral arc of the form:

$$R = [e^{k\theta}]_{\theta_{start}}^{\theta_{finish}}$$

where R is the vector radius, K is the parameter, θfinish is the polar angle of the vector radius corresponding to the end of the arc on the spiral and θstart is the polar angles of the vector radius corresponding to the start of the arc on the spiral, and the generatrices bearing on one directrix and passing through two possibly diametrically opposed point on the directrix, are logarithmic spiral arcs, the spirals of the curved axis and the two generatrices having the same pole and the spiral arcs of the axis and the two generatrices having the same θf and θs, the lengths of the vector radii of the three spirals being, for the same angle θ, such that R1>R2>R3, R2 being the vector radius of the longitudinal curved axis and R1 and R3 being those of the two generatrices under consideration.

In this way, a curved anchoring zone is obtained which is better able to adapt to the inner wall of, for example, a femoral shaft and which, nevertheless, makes it possible to form an optimized series of anchoring rods, each rod having an identical fixing zone, the sizes of the anchoring zones of the rods of the optimized series being progressively larger and thicker, characterized in that the anchoring zones of two consecutive rods of increasing size are such that the θstart of the first is less than the θstart of the second and the θfinish of the first is less than the θfinish of the second, but the θfinish of the first is greater than the θstart of the second.

It is thus possible to choose and to introduce the appropriate rod into the prepared femoral shaft to ensure that the fixing portion is at the required distance from the proximal end of the femoral shaft. In this way, the remaining proximal part of the prosthesis can be assembled, without having to reshape the femoral shaft, as all the rods in the optimized series fit well.

The proximal zone may be a fixing zone to which the proximal module is well adapted. The proximal zone may also be the zone which takes the place of the proximal module, when an all-in-one prosthetic component is used.

BRIEF DESCRIPTION OF THE DRAWING

In the accompanying drawings, which are provided solely by way of example:

FIG. 4 illustrates an optimized series of anchoring rods according to the invention, FIG. 5 illustrates the assembly of a rod in a prepared femoral shaft.

DESCRIPTION OF THE PREFERRED EMBODIMENT

Figures 1, 2:
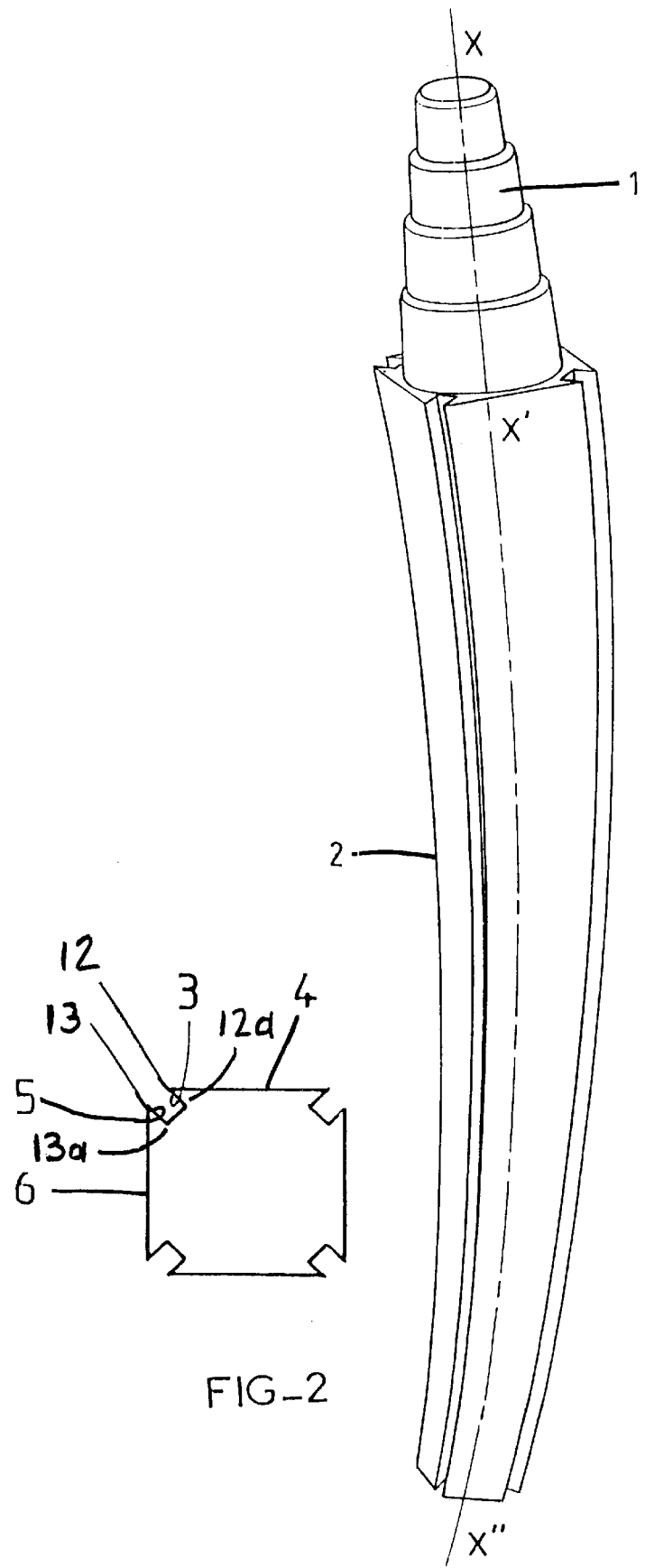
FIG. 1 is a perspective view of an anchoring rod according to the invention.
FIG. 2 is a transverse section through the anchoring zone of the rod in FIG. 1.

The anchoring rod shown in FIGS. 1 and 2 comprises a proximal zone 1 consisting of four superimposed cones of axis XX' extended by an anchoring zone 2 of curved axis X'X".

The cross section of the anchoring zone 2 is substantially square in this simplified example; the sides of the square thus form between them an angle of 90° except that, at each apex 12, 13 corresponding to the fins 12a, 13a, a recess is provided according to the invention. The recess in the upper left corner of the cross-section of the anchoring zone 2 as shown in FIG. 2 has opposed sides 3 and 5, and each fin 12a and 13a is formed by a dihedron provided by the intersection of the adjacent sides of the anchoring zone and recess, i.e., sides 4, 3 and sides 6, 5. The two most remote sides 4 and 6 of the dihedra of the pair of fins 12a, 13a form an angle of from 60° to 120°, e.g., 90° in the illustrated anchoring zone 2. This angular relationship between sides 4 and 6 is applicable to the extents or portions of the remote sides 4 and 6 extending a distance only in the order of one millimeter from the adjacent fin (i.e., fins 12a and 13a respectively). In other words, the one millimeter length is measured from each fin 12a, 13a along the surfaces of the respective sides 4, 6 in a plane passing through the axis of the anchoring zone at a right angle as illustrated in FIG. 2. After this length, the sides 4, 6 may have any curvature or geometry. The illustrated geometry of the sides 4, 6 is a flat surface. Also, the side 3 of the recess adjacent to a side 4 of the cross section forms an acute angle of less than 60° therewith, i.e. a cutting edge.

The two sides 3, 5 of the same recess form an angle of 0° between them, i.e. the recess does not widen out inwardly. In another embodiment (not shown) the recess may widen outwardly.

Similarly, the side 5 of the recess adjacent to the side 6 of the transverse section also constitutes a cutting edge.

Figure 3:
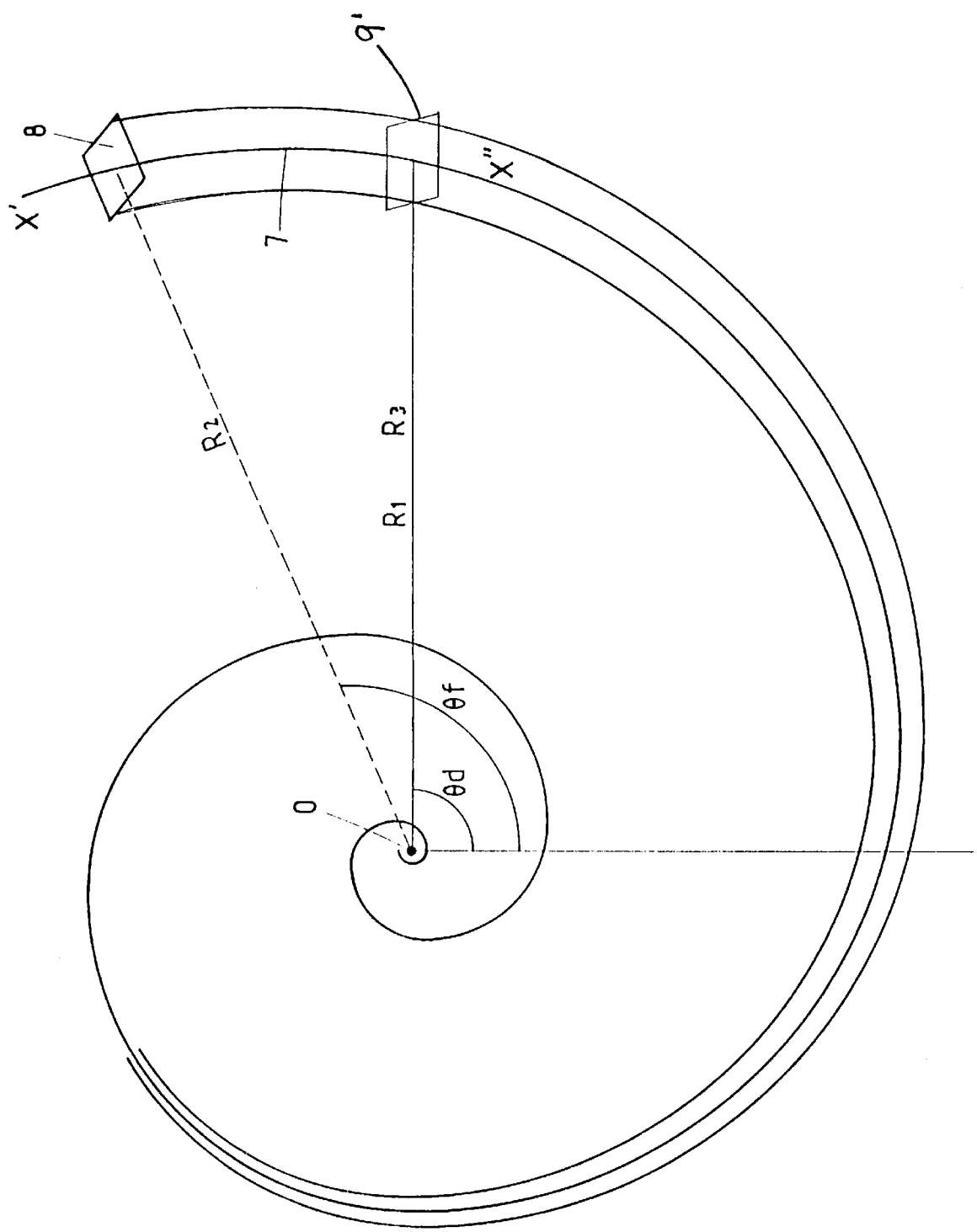
FIG. 3 is a diagram illustrating an anchoring rod according to the invention.

The curved longitudinal axis X'X'' of the anchoring zone 2 extends along a logarithmic spiral arc 7 (FIG. 3) of the formula:

$$R_2 = [e^{k_2 \theta}]_{\theta_{start}}^{\theta_{finish}}$$

in which R2 is the vector radius, K2 the parameter, θfinish the angle of the vector radius corresponding to the end of the arc on the spiral of θstart the angle of the vector radius corresponding to the start of the arc on the spiral. Similarly, the generatrices 8 bearing on the directrix 9' which, in this instance, is square and corresponds to the cross section of the rod, are logarithmic spiral arcs of vector radii R1 and R3, the three logarithmic spirals having a common pole 0 and R1>R2>R3, K1, K2 and K3 being selected accordingly.

FIG. 4 shows three rods 9, 10, 11 of an optimized series of anchoring rods.

The anchoring zones are progressively larger and progressively thicker from rod 9 to rod 10 and rod 10 to rod 11, while the fixing zones are identical. The anchoring zones of two consecutive rods 10, 11 of increasing size are such that the θstart of the rod 10 is less than the θstart of the rod 11, but the θfinish of the rod 10 is greater than the θstart of the rod 11.

Figure 6:
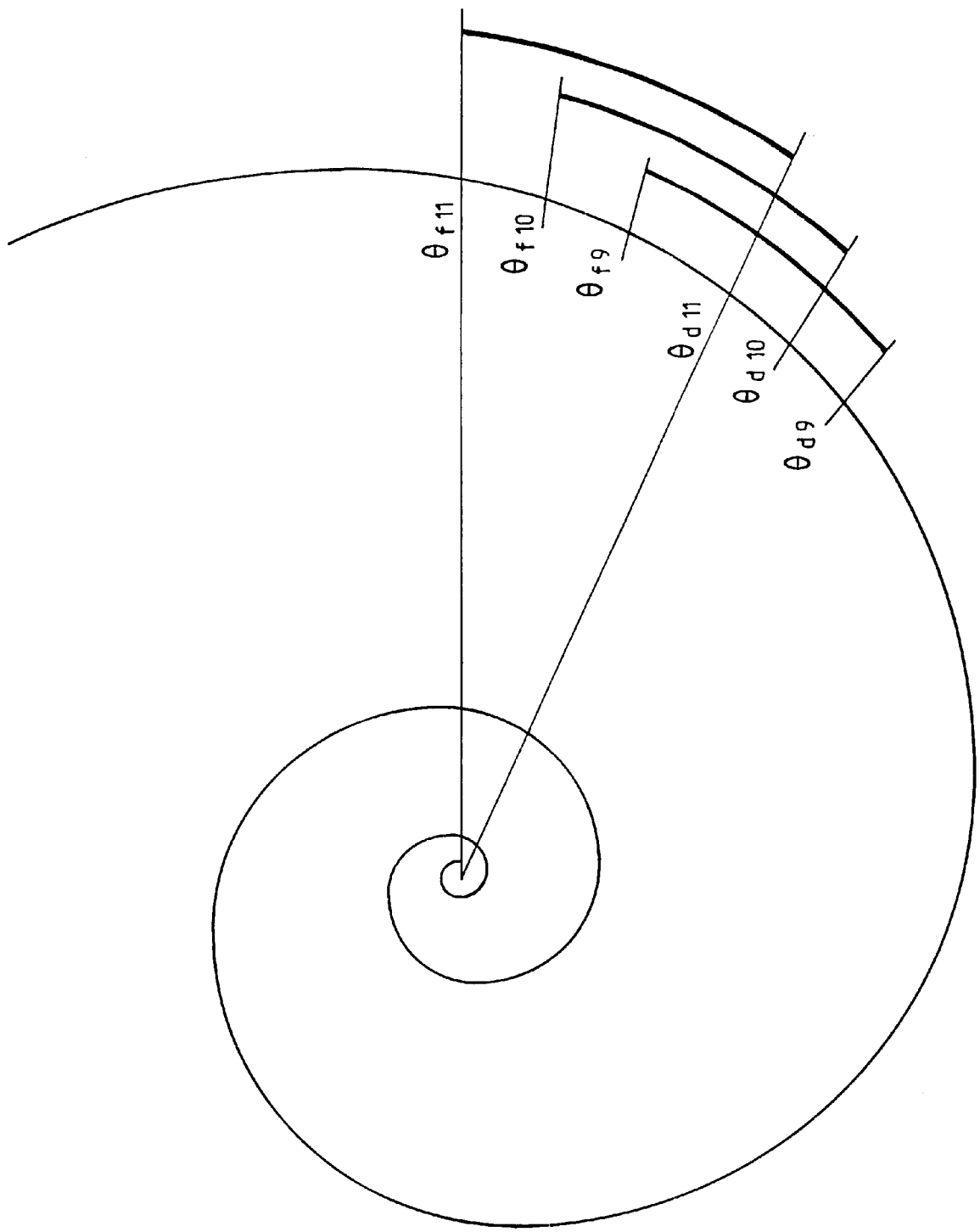
FIG. 6 is a diagram illustrating the method of producing an optimized series of anchoring rods according to the invention.

The logarithmic spiral arcs taken to constitute the three rods in the series are diagrammatically shown in FIG. 6.

FIG. 5 shows that any one of the rods, e.g. the rod 9, may be inserted in the femoral shaft F so that the fixing zone is in the desired position for receiving the proximal module of a prosthesis.

I claim:

1. A prosthesis anchoring rod comprising a proximal zone and an axial anchoring zone having a longitudinal axis, wherein the anchoring zone has a cross-section including a plurality of peripheral sides extending between at least two pairs of cutting fins, each pair of cutting fins including spaced fins having a single recess therebetween, the recess including opposed sides, each fin being formed by a dihedron provided by the intersection of adjacent sides of the cross-section and the opposed sides of the recess, the adjacent side and opposed side forming each dihedron intersecting at an angle of less than 60° and forming an apex, the apex being a cutting edge, the two most remote sides of the dihedra of each pair of fins forming an angle equal to from 60° to 120° to thereby provide a remote side angular relationship, the remote side angular relationship being applicable to the extents of the remote sides extending a distance of substantially one millimeter from the fins measured from each fin along the surface of the respective sides in a plane passing through the longitudinal axis at a right angle.

2. The prosthesis anchoring rod according to claim 1, wherein the anchoring zone has a longitudinal length, and the fins extend along substantially the entire longitudinal length of the anchoring zone.

3. The prosthesis anchoring rod according to claim 1, wherein the fins are substantially parallel to the anchoring zone longitudinal axis.

4. The prosthesis anchoring rod according to claim 1, wherein the fins have apexes are equidistant from the anchoring zone longitudinal axis as measured in a plane passing through the axis at a right angle.

5. The prosthesis anchoring rod according to claim 1, wherein the anchoring zone has a longitudinal length, and a cross-sectional angular orientation of the fin relative to the longitudinal axis is constant along the longitudinal length of the anchoring zone.

6. The prosthesis anchoring rod according to claim 1, wherein the longitudinal axis of the anchoring zone is curved and extends along a logarithmic spiral arc of formula:

$$R = [e^{k\theta}]_{\theta_{start}}^{\theta_{finish}}$$

where R is a vector radius, K is a parameter, θfinish is a polar angle of the vector radius corresponding to the end of the spiral arc and θstart is a polar angle of the vector radius corresponding to the start of the spiral arc, and generatrices bearing on one directrix and passing through two points on either side of the directrix are also logarithmic spiral arcs, the spiral arcs of the longitudinal axis and the two generatrices having a common pole, the spiral arcs of the two generatrices having θfinish and θstart values corresponding with those of the longitudinal axis, and the spiral arcs of the two generatrices and the longitudinal axis each having a vector radius length for a selected same polar angle, θsame, such that the vector radius length for one of the generatrices is less than the vector radius length of the longitudinal axis and the vector radius length of the other of the generatrices is greater than the vector radius length of the longitudinal axis at the polar angle θsame.

7. The prosthesis anchoring rod according to claim 1, wherein the peripheral sides of the anchoring zone cross-section are substantially flat.

8. The prosthesis anchoring rod according to claim 1, wherein the anchoring zone cross-section has a substantially polygon shape and the pairs of cutting fins are located at corners of the polygon shape.

9. The prosthesis anchoring rod according to claim 8, wherein the opposed recess walls are substantially parallel, the anchoring zone has a longitudinal length, and the fins extend substantially the entire longitudinal length of the anchoring zone.

10. The prosthesis anchoring rod according to claim 1, wherein the anchoring zone cross-section has a substantially rectangular shape and the pairs of cutting fins are located at each corner of the rectangular shape.

11. The prosthesis anchoring rod according to claim 10, wherein the anchoring zone has a longitudinal length, and the fins extend along substantially the entire longitudinal length of the anchoring zone.

12. An optimized series of prosthesis anchoring rods, wherein each rod comprises a proximal zone and an axial anchoring zone having a longitudinal axis, the anchoring zone has at least two pairs of cutting fins, the proximal zone of each rod having a fixing zone of identical shape and size, the sizes of the anchoring zones of the rods in the series being progressively larger and progressively thicker, characterized in that the anchoring zone longitudinal axis is curved and extends along a logarithmic spiral arc of formula:

$$R = [\, e^{k\theta} \,]_{\theta_{start}}^{\theta_{finish}}$$

where R is a vector radius, K is a parameter, θfinish is a polar angle of the vector radius corresponding to the end of the spiral arc and θstart is a polar angle of the vector radius corresponding to the start of the spiral arc, and two consecutive rods of increasing size are such that the θstart of the first is less than the θstart of the second and the θfinish of the first is less than the θfinish of the second, the θfinish of the first is greater than the θstart of the second, each anchoring zone having a cross-section including a plurality of peripheral sides extending between the two pairs of cutting fins, each pair of cutting fins including paced fins having a recess therebetween, the recess including opposed sides, each fin being formed by a dihedron provided by the intersection of adjacent sides of said cross-section and recess, the two most remote sides of the dihedra of each pair of fins forming between them an angle equal to substantially 90° to thereby provide a remote side angular relationship, the remote side angular relationship being applicable to the extents of the remote sides extending a distance of one millimeter from the fins measured from each fin along the surfaces of the respective sides in a plane passing through the longitudinal axis at a right angle.

13. An optimized series of prosthesis anchoring rods, wherein each rod comprises a proximal zone and an axial anchoring zone having a longitudinal axis, the anchoring zone has at least two pairs of cutting fins, the proximal zone of each rod having a fixing zone of identical shape and size, the sizes of the anchoring zones of the rods in the series being progressively larger and progressively thicker, characterized in that the anchoring zone longitudinal axis is curved and extends along a logarithmic spiral arc of formula:

$$R = [\, e^{k\theta} \,]_{\theta_{start}}^{\theta_{finish}}$$

where R is a vector radius, K is a parameter θfinish is a solar angle of the vector radius corresponding to the end of the spiral arc and θstart is a polar angle of the vector radius corresponding to the start of the spiral arc, and two consecutive rods of increasing size are such that the θstart of the first is less than the θstart of the second and the θfinish of the first is less than the θfinish of the second, the θfinish of the first is greater than the θstart of the second, each anchoring zone having a cross-section including a plurality of peripheral sides extending between the two pairs of cutting fins, each pair of cutting fins including spaced fins having a recess therebetween, the recess including opposed sides, each fin being formed by a dihedron provided by the intersection of adjacent sides of said cross-section and recess, the two most remote sides of the dihedra of each pair of fins forming between them an angle equal to from 60° to 120° to thereby provide a remote side angular relationship, the remote side angular relationship being applicable to the extents of the remote sides extending a distance of one millimeter from the fins measured from each fin along the surfaces of the respective sides in a plane passing through the longitudinal axis at a right angle.

14. The optimized series of prosthesis anchoring rods according to claim 13, wherein the peripheral sides of the anchoring zone cross-section are substantially flat.

15. The optimized series of prosthesis anchoring rods according to claim 13, wherein the anchoring zone cross-section has a polygon shape and the pairs of cutting fins are located at corners of the polygon shape.

16. The optimized series of prosthesis anchoring rods according to claim 13, wherein the anchoring zone cross-section has a substantially rectangular shape and the pairs of cutting fins are located at each corner of the rectangular shape.

17. The optimized series of prosthesis anchoring rods according to claim 13, wherein each anchoring zone has a longitudinal length, and the fins extend along substantially the entire longitudinal length of the anchoring zone.

\* \* \* \* \*

UNITED STATES PATENT AND TRADEMARK OFFICE
CERTIFICATE OF CORRECTION

PATENT NO. : 5,928,289
DATED : July 27, 1999
INVENTOR(S) : Andre Georges Deckner It is certified that error appears in the above-indentified patent and that said Letters Patent is hereby corrected as shown below:

Column 4, line 2, (claim 1, line 8) after "of" insert --an--.

Column 4, line 2, (claim 1, line 8) delete "sides" and insert --side--.

Column 4, line 3, (claim 1, line 9) delete "the" (first occurrence), and insert --an--.

Column 4, line 3, (claim 1, line 9) delete "sides" and insert --side--.

Column 6, line 8, (claim 13, line 13) delete "solar" and insert --polar--.

Add the following claim.

--18. Anchoring rod according to claim 1, wherein each of the opposed sides of the recess of the dihedra forming the pair of fins is in a plane that passes substantially through the anchoring zone longitudinal axis.--

Signed and Sealed this

Twenty-ninth Day of August, 2000

*Attest:*

Q. TODD DICKINSON

*Attesting Officer*     *Director of Patents and Trademarks*